(12) United States Patent
Ben-Yair et al.

(10) Patent No.: US 10,169,342 B1
(45) Date of Patent: **\*Jan. 1, 2019**

(54) FILTERING DOCUMENT SEARCH RESULTS USING CONTEXTUAL METADATA

(71) Applicant: International Business Machines Corporation, Armonk, NY (US)

(72) Inventors: Yoav Ben-Yair, Mevasseret Zion (IL); Gil Fuchs, Mevasseret Zion (IL); Itai Gordon, Modiin (IL); Ilan D. Prager, Beit Shemesh (IL)

(73) Assignee: International Business Machines Corporation, Armonk, NY (US)

( \* ) Notice: Subject to any disclaimer, the term of this patent is extended or adjusted under 35 U.S.C. 154(b) by 0 days.

This patent is subject to a terminal disclaimer.

(21) Appl. No.: 15/910,129

(22) Filed: Mar. 2, 2018

Related U.S. Application Data

(63) Continuation of application No. 15/637,037, filed on Jun. 29, 2017.

(51) Int. Cl.
*G06F 17/30* (2006.01)
*G06K 9/00* (2006.01)
*A61B 5/11* (2006.01)

(52) U.S. Cl.
CPC ...... *G06F 17/30011* (2013.01); *A61B 5/1114* (2013.01); *G06F 17/30525* (2013.01); *G06F 17/30864* (2013.01); *G06F 17/30991* (2013.01); *G06F 17/30997* (2013.01); *G06K 9/00315* (2013.01)

(58) Field of Classification Search
CPC ......... G06F 17/30011; G06F 17/30525; G06F 17/30864; G06F 17/30991; G06F 17/30997; G06F 17/30315; A61B 5/1114; G06K 9/00315

USPC ................................ 707/722, 732, 754, 758
See application file for complete search history.

(56) References Cited

U.S. PATENT DOCUMENTS

| 9,087,081 | B2 | 7/2015 | Cao et al. |
| 9,298,712 | B2 | 3/2016 | Velagapudi et al. |
| 2008/0077571 | A1 | 3/2008 | Harris et al. |
| 2008/0097979 | A1 | 4/2008 | Heidloff et al. |
| 2010/0085446 | A1 | 4/2010 | Thorn |
| 2013/0054576 | A1\* | 2/2013 | Karmarkar ........ G06F 17/30861 707/722 |
| 2013/0054622 | A1 | 2/2013 | Karmarkar et al. |
| 2015/0213123 | A1 | 7/2015 | Peters et al. |

(Continued)

OTHER PUBLICATIONS

Ben-Yair et al. Original U.S. Appl. No. 15/637,037, filed Jun. 29, 2017.

(Continued)

*Primary Examiner* — Hares Jami
(74) *Attorney, Agent, or Firm* — Stephen R. Yoder; William H. Hartwell

(57) ABSTRACT

Receiving contextual data including a facial movement associated with an active document. A response associated with the active document is detected and associated with the received contextual data. A contextual metadata tag is generated based on the detected response to the active document. A contextual keyword is created that corresponds to the contextual metadata tag. Search results received in response to the query are filtered based on the contextual metadata tag.

1 Claim, 7 Drawing Sheets

(56) References Cited

U.S. PATENT DOCUMENTS

2017/0091534 A1    3/2017  Venkataraman et al.
2018/0089241 A1*   3/2018  Mendels ........... G06F 17/30312

OTHER PUBLICATIONS

Buscher et al., "Attentive Documents: Eye Tracking as Implicit Feedback for Information Retrieval and Beyond", Journal ACM Transaction on Interactive Intelligent Systems (TiiS) archive vol. 1 Issue 2, Jan. 2012, 30 pages, <http://dl.acm.org/citation.cfm?id=2070722>.

Miller et al., "Attention-Based Information Retrieval Using Eye Tracker Data", Copyright is held by the author/owner(s), K-CAP'05, Oct. 2-5, 2005, Banff, Alberta, Canada, pp. 209-210.

Mell et al., "The NIST Definition of Cloud Computing Recommendations of the National Institute of Standards & Technology", Special Publication 800-145, Sep. 2011. Gaithersburg, MD, 7 pages.

Nadeem, "is there an open source software available for facial emotion detection in real time?", Mar. 30, 2015, 4 pages, <https://www.researchgate.net/post/is_there_an_open_source_software_available_for_facial_emotion_detection_in_real_time>.

Wang et al., "Explore Eye Movement Patterns in Search Result Evaluation and Individual Document Evaluation", Nov. 2015, 4 pages, <http://onlinelibrary.wiley.com/doi/10.1002/pra2.2015.1450520100144/pdf>.

IBM, Appendix P, List of IBM Applications or Patents Treated as Related, dated Jun. 19, 2018, 2 pages.

* cited by examiner

US 10,169,342 B1

FILTERING DOCUMENT SEARCH RESULTS USING CONTEXTUAL METADATA

BACKGROUND

The present invention relates to filtering document search results and more specifically to filtering document search results using contextual metadata.

Metadata-based media searches are known. Typically, metadata associated with media content is based on the type of content or the objects within displayed content. Metadata is captured for searching/locating the content or objects in digital storage. Media, as used herein, refers to various content formats including print media (such as books, magazines, and newspapers), television, movies, video games, music, cell phones, software, and the Internet. Media content, or simply content, is delivered to users through media.

SUMMARY

In one aspect of the present invention, a method, a computer program product, and a system includes: receiving contextual data comprising a facial movement associated with an active document, detecting a response associated with the active document based on the received contextual data, generating a contextual metadata tag based on the detected response to the active document, receiving a query comprising a contextual keyword corresponding to the contextual metadata tag, filtering search results received in response to the query based on the contextual metadata tag, and displaying a list of the filtered search results.

DETAILED DESCRIPTION

Figure 1:
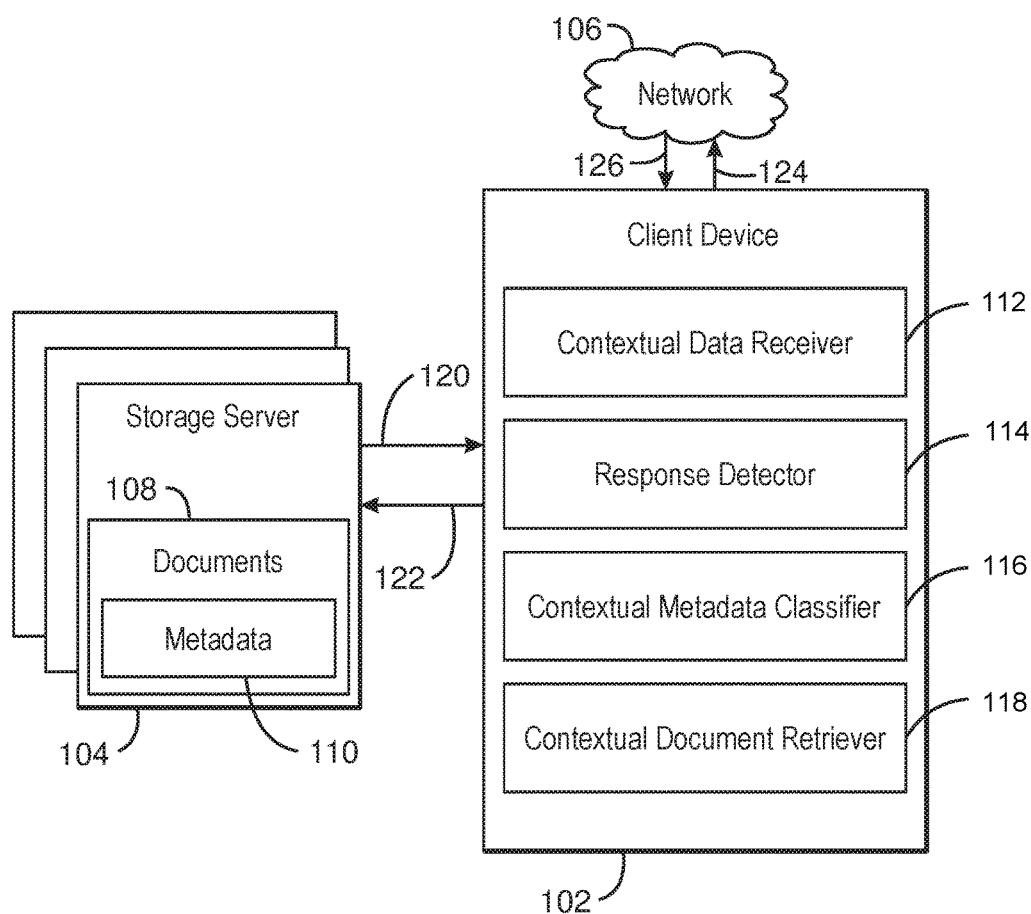
FIG. 1 is a block diagram of an example system that can filter document search results using contextual metadata.

Some embodiments of the present invention recognize that the context in which a user views media such as email serves as an additional way in which the media may be located via search. That is, the user who views media may recall more readily the context, or the circumstances surrounding the viewing event, than the particular content or objects within the media.

According to an embodiment described herein, a system can include a processor to receive contextual data comprising a facial movement associated with an active document. The processor can also further detect a response associated with the active document based on the received contextual data. The processor can also generate a contextual metadata tag based on the detected response to the active document. The processor can further receive a query comprising a contextual keyword corresponding to the contextual metadata tag. The processor can further also filter search results received in response to the query based on the contextual metadata tag. The processor can also display a list of the filtered search results.

According to another embodiment described herein, a method can include receiving, via a processor, contextual data comprising a facial movement associated with an active document. The method can also further include detecting, via the processor, a response associated with the active document based on the received contextual data. The method can also include generating, via the processor, a contextual metadata tag based on the detected response to the active document. The method can further include receiving, via the processor, a query comprising a contextual keyword corresponding to the contextual metadata tag. The method can also include filtering, via the processor, search results received in response to the query based on the contextual metadata tag. The method can also further include displaying, via the processor, a list of the filtered search results.

According to another embodiment described herein, a computer program product for filtering document search results can include computer-readable storage medium having program code embodied therewith. The computer readable storage medium is not a transitory signal per se. The program code is executable by a processor to cause the processor to receive contextual data comprising a facial movement associated with an active document. The program code can also cause the processor to detect a response associated with the active document based on the received contextual data. The program code can also cause the processor to generate a contextual metadata tag based on the detected response to the active document. The program code can also cause the processor to receive a query comprising a contextual keyword corresponding to the contextual metadata tag. The program code can also cause the processor to also further filter search results received in response to the query based on the contextual metadata tag. The program code can also cause the processor to also display a list of the filtered search results.

Search engines enable users to find documents or emails using keywords that are generally related to content. Some search engines also allow users to sort documents or emails based on a time and a date. However, sometimes a user wants to retrieve a document or email, but only remembers an action they were performing at the time the document or email was read or created. For example, the user only remembers where they were or how they felt when they were reading a document rather than what was actually written in the document. In addition, in some instances, there are many documents with similar keywords related to content and thus finding a particular document based on subject matter alone is difficult for the user.

For example, a user wants to find an email about the result of a case, but does not remember details such as the participants, the date, or the subject of the case. However, the user remembers the context of reading the email. For example, the user remembers being amazed by the email and reading the email several times to be sure about the result of the project. As discussed herein, the context in which a user receives media content is a physical context of the user while viewing the content. Physical contexts include for example: (i) movement of hands; (ii) movement of eyes; (iii) posture of the user—standing, sitting; (iv) motion of the body—walking, running; (v) location of the user; (vi) facial expressions; (vii) identities of people proximate the user; and/or (viii) environmental characteristics.

According to some embodiments of the present invention, a processor filters document search results using contextual metadata. In one example, the processor receives contextual data including a facial movement associated with an active document. As used herein, an active document refers to an electronic document being actively read from or written to. In another example, the facial movement includes eye movement. In yet another example, the document is displayed in a foreground of a device display. The processor detects a response associated with the active document based on the received contextual data. In one example, the detected response is an emotional response to reading the active document. The processor generates a contextual metadata tag based on the detected response to the active document. The processor receives a query including a contextual keyword corresponding to the contextual metadata tag. The processor filters the search results received in response to the query based on the contextual metadata tag. The processor displays a list of filtered search results. Accordingly, some embodiments of the present invention present a filtered set of document search results using contextual metadata. In some embodiments, users are presented with options for filtering document search results based on context. In one example, a user chooses from different categories of context to narrow down the total amount of search results based on the context that the user remembers. In that way, some embodiments of the present invention enable users to query documents based on the actions or emotions experienced while reading those documents.

Some embodiments of the present invention are implemented in a cloud computing environment. As discussed in more detail below in reference to at least FIGS. 4, 5, and 6, a computing device configured to filter document search results using contextual metadata may be implemented in a cloud computing environment. It is understood in advance that although this disclosure includes a description of cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based email). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

FIG. 1 is a block diagram of an example system that can filter document search results using contextual metadata. The system is generally referred to using the reference number 100 and can be implemented at least in part using the computing device 400 of FIG. 4 below.

Example system 100 includes a client device 102, storage servers 104, and a network 106. The storage servers 104 store documents 108, including metadata 110. The client device 102 includes a contextual data receiver 112, a response detector 114, a contextual metadata classifier 116, and a contextual document retriever 118. In one embodiment, the contextual document retriever 118 is a search engine for retrieving documents based on contextual data. The client device 102 stores and accesses data with the storage servers 104 as indicated by arrows 120 and 122. The client device 102 sends data to and receives data from the network 106 as indicated by arrows 124 and 126, respectively.

In the example system 100, the contextual data receiver 112 receives contextual data from the network 106 or the client device 102. In this example, the contextual data includes eye tracking information received from an eye tracking component. In some embodiments of the present invention, the eye tracking component is included in the client device 102. In some embodiments of the present invention, the eye tracking component is a separate device that tracks user eye movements when the user is reading and sends the tracking information to the client device 102 via the network 106. In some examples, the contextual data includes facial expression recognition data. For example, a face expression recognition engine detects one or more facial expressions from images received of the face of a user while reading a document. According to some embodiments of the present invention, the document is a word processor document, an email, or a spreadsheet. In some examples, the contextual data includes contextual information from the client device 102. In some examples, the contextual data receiver 112 receives metadata about emails or other documents that were read before and after the active document so that this information can be used to filter results later on. For example, the user remembers the details of a document read before or after a document to be retrieved. The user includes this information in the query to reduce the number of results returned. According to some embodiments of the present invention, the contextual information includes time, date, and global positioning satellite (GPS) data corresponding to the time a document is an active document on a device. In some embodiments of the present invention, the system 100 records and analyzes what the user is doing or feeling while reading or editing an active document, so that later the user is able to search based on what the user is doing or feeling as discussed in more detail below.

In some examples, the response detector 114 detects a response associated with an active document. For example, the active document is open and a user is reading the active document and the user experiences a physical response while reading the active document. An example physical response is that the user reads a specific portion of the active document multiple times. In other examples, the user reads the active document slowly or quickly. In one example, when the user is reading a document or email, an eye movement tracker (not shown) tracks his eyes in order to store and later analyze those parts of the text at which the user is looking. The response detector 114 analyzes reading patterns and saves the analysis data and/or results of the analysis. As mentioned above, the contextual data receiver 112 also records the location of the device periodically using GPS or other techniques and saves the time when the user was reading the document. In some examples, the contextual data receiver 112 receives captured images of the face of the reader from a camera and the response detector 114 extracts actions that the user was performing when reading the text.

In some examples, the captured images are analyzed using any suitable techniques and saved to storage. For example, after the contextual data is stored, the contextual metadata classifier 116 classifies the raw contextual data into categories that may be used to ease the document search later. For example, if a location of the user is changed while reading, contextual metadata classifier 116 classifies the reading as reading-while-moving. In some examples, the contextual metadata classifier 116 classifies contextual data as long reading or short reading. In some examples, the contextual metadata classifier 116 analyzes unusual behavior by the user. For example, the unusual behavior includes reading minor parts of the email. Other examples of unusual behavior include: (i) reading the same part of an email again and again; (ii) reading the active document during a specific time. For example, the metadata classifier 116 notes that the document was read during a holiday. In some examples, by analyzing the face pictures and the eye tracking data, the contextual metadata classifier 116 detects a user mood and adds appropriate tags into the metadata of the document. For examples of a detected user mood include: (i) being nervous, (i) being amused, (iii) being surprised, and/or (iv) being angry.

Some embodiments of the present invention provide for when a user is searching for documents and types text in a document and the user also specifies text and/or tags about what happened when reading. For example, the user specifies that the reading was a long reading during a holiday morning. In some examples, the user specifies that the user is shocked by an email after the user reads a lot of emails. As another example, the user remembers reading an email about a company's shares after reading a very long email about the company's re-organization. In some examples, the process is iterative. For example, if the system recognizes that too many results are returned in response to a query, the system suggests using more tags to reduce and to focus the search results based on what the user did when reading.

In some examples, the contextual document retriever 118 includes an analytics engine in order to map the searched text into the metadata that was saved. For example, a user specifies that the user is reading during a trip to Asia one morning. The contextual document retriever 118 maps saved locations onto a continent and records the time as a local time.

For example, a user may want to find an email about the certain result of a project, but the user does not remember the participants of the project, when the email was last read, and the subject of the email. In this example, the user only remembers being amazed by the email and reading the email several times to be sure about the result. The user invokes system 100, which recorded the physical actions when reading the email. For example, the user specifies reading the email several times and that the time was in the morning when searching for the email. In response to the filtered search, the user receives only a few emails, much reduced from the number being searched. However, the user remembers holding his head when reading the email and enters that he was holding his head as a search criteria for the contextual document retriever 118. The resulting document search result may have only one email to present, which may be the email that the user is looking for.

It is to be understood that the block diagram of FIG. 1 is not intended to indicate that the system 100 is to include all of the components shown in FIG. 1. Rather, the system 100 can include fewer or additional components not illustrated in FIG. 1 (e.g., additional client devices, storage servers, networks, documents, contextual information, etc.).

Figure 2:
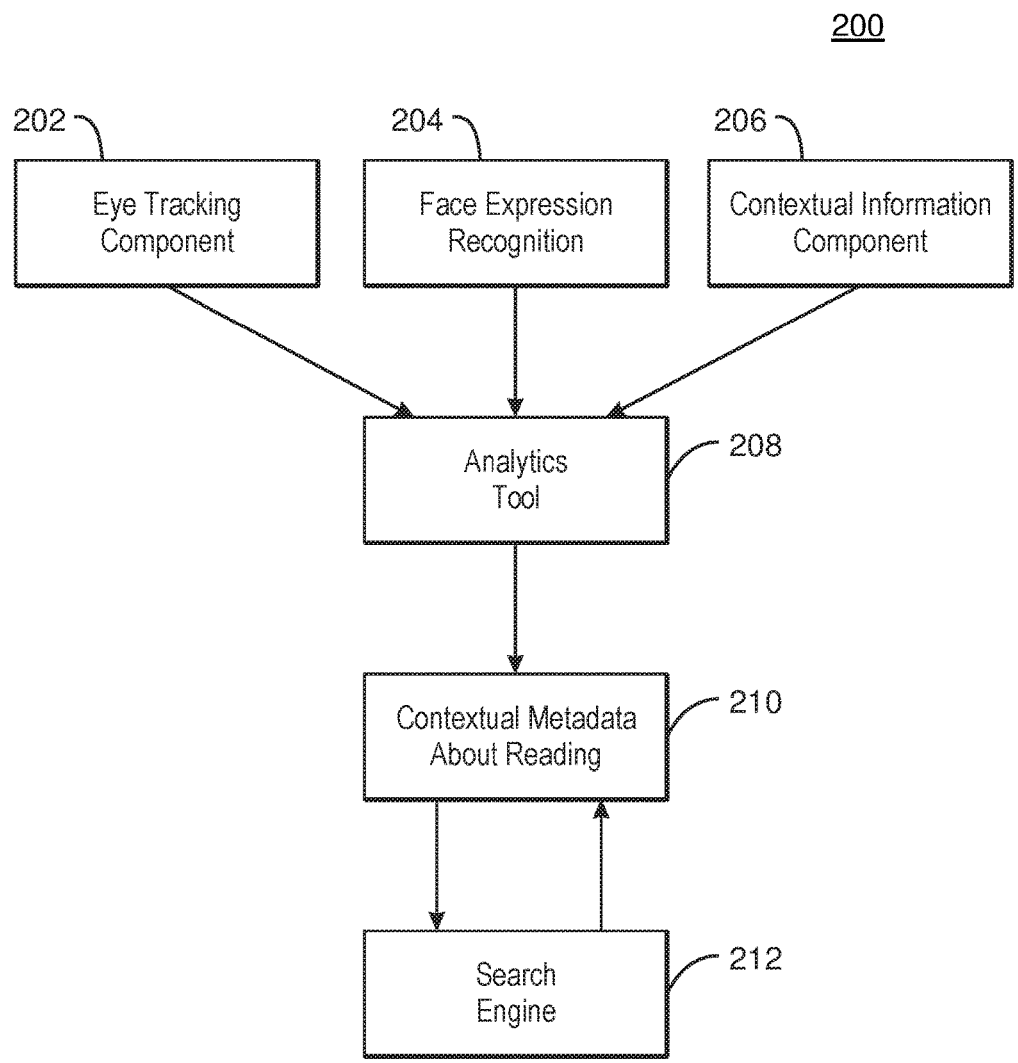
FIG. 2 is an information flow diagram of an example system that can filter document search results using contextual metadata.

FIG. 2 is an information flow diagram of an example system that can filter document search results using contextual metadata. The system 200 can be implemented with any suitable computing device, such as the computing device 400 of FIG. 4. For example, the client device may be the computing device 400.

As shown in FIG. 2, the system 200 includes an eye tracking component 202, a face expression recognition component 204, and a contextual information component 206 that receives contextual information from a device.

In some examples, the analytics tool 208 receives contextual data from the eye tracking component 202, the face expression recognition component 204, and the contextual information component 206 while a document is active. For example, a user may be reading or editing the active document. The analytics tool 208 analyzes the contextual data. In some examples, the analytics tool 208 can extract reading patterns from the contextual data. For example, the reading patterns are extracted from eye movements or face images. In some examples, the analytics tool 208 can extract user feelings or moods from the contextual data. For example, the analytics tool 208 can detect that a user is angry, nervous, excited, or other exhibiting any other mood, based on the contextual data.

In some examples, the extracted reading patterns and moods are used to generate contextual metadata tags 210 about the reading. For example, mood tags indicate the mood of a user while reading an active document. In other embodiments, movement tags indicate that a device was moving while the active document was being read.

In some examples, the metadata tags are used to filter search results when searching for a document using the search engine 212. For example, the search engine 212 receives a query with text and a keyword corresponding to a contextual metadata tag. In some examples, the search engine 212 receives a query and detects that the number of search results returned in response to the query exceeds a predetermined threshold number of search results. The search engine 212 accordingly suggests a plurality of metadata tag categories for a user to select one or more contextual metadata keywords. The search engine 212 receives one or more metadata keywords and filter the search results using the corresponding contextual metadata tags. The resulting filtered search results may be easier to browse through and find a particular document.

It is to be understood that the block diagram of FIG. 2 is not intended to indicate that the system 200 is to include all of the components shown in FIG. 2. Rather, the system 200 can include fewer or additional components not illustrated in FIG. 2 (e.g., additional sources of contextual data, analytics tools, search engines, etc.). The information flow diagram of FIG. 2 is not intended to indicate that the operations of the system 200 are to be executed in any particular order, or that all of the operations of the system 200 are to be included in every case. Additionally, the system 200 may perform any suitable number of additional operations.

Figure 3:
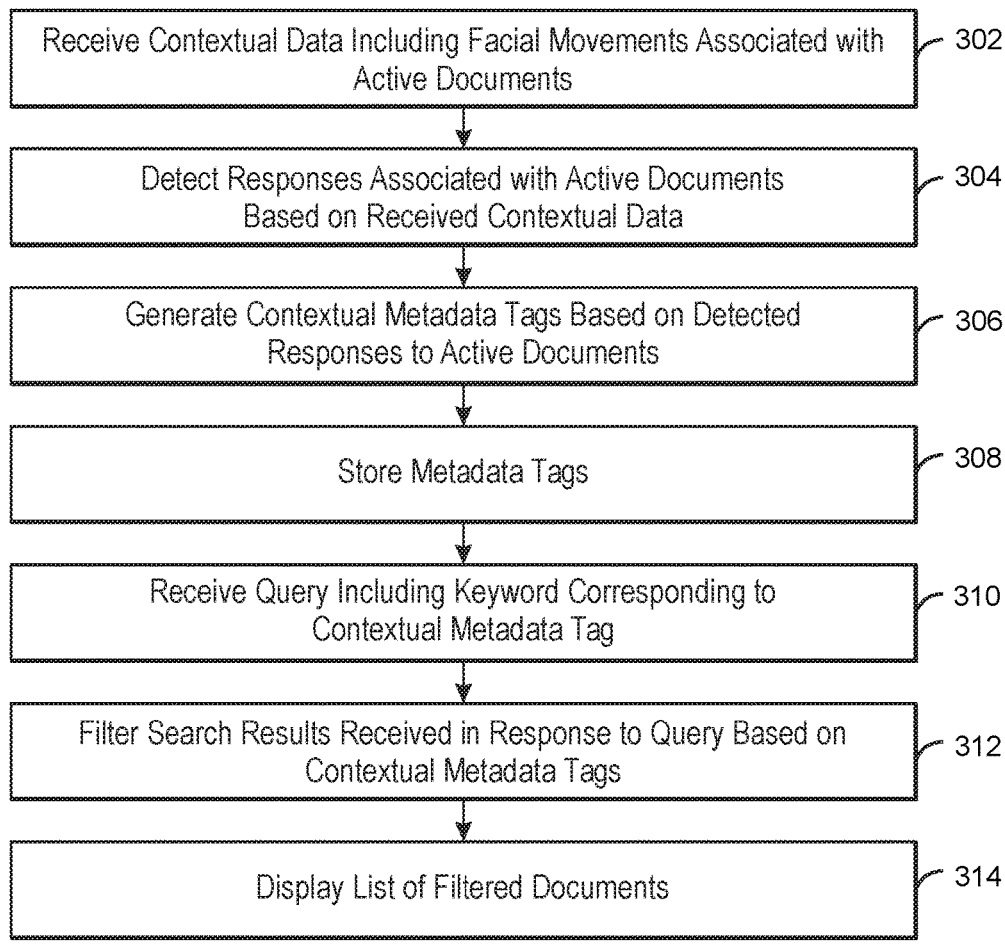
FIG. 3 is a process flow diagram of an example method that can filter document search results using contextual metadata.

FIG. 3 is a process flow diagram of an example method that can filter document search results using contextual metadata. The method 300 can be implemented with any suitable computing device, such as the computing device 400 of FIG. 4. For example, the method can be implemented via the processor 402 of computing device 400.

At block 302, a processor receives contextual data including facial movements associated with active documents. For example, an active document may be in a foreground of a device and may be read or written to by a user. In some examples, the contextual data may include a received image of a face of a user reading the active document. In some examples, the contextual data may include facial features or movements including eye movement, eyebrow movement, different eye features, a change to the nose position in relation to a face, opening of the mouth, catching of the head with hands, etc. For example, eye features may include closing of the eyes, squinting, wide opening of the eyes, etc. In some examples, the contextual data may also include a location and a time associated with the active document. In some examples, the contextual data collection may be a preference or setting that can be adjusted by a user. For example, a user can adjust privacy settings to prevent a collection of the contextual data.

At block 304, the processor detects a response associated with the active document based on the received contextual data. For example, the processor may detect a facial expression based on the contextual data. In some examples, the processor may detect an emotional response based on the contextual data. In some examples, the emotional response can be detected based on the shape or position of the mouth, nose, eyebrows, and facial lines in the forehead in relation to one another. For example, a response of sadness may be detected based on display upwardly slanted eyebrows and a frown. In some examples, a response of happiness may be detected based on a smile and a crescent-shaped eye. In some examples, a response of anger may be detected based on eyebrows squeezed together to form a crease, and eyelids that are tight and straight. In some examples, anger may also be based on the head being detected as slightly lowered as the eyes look through a lowered brow.

At block 306, the processor generates a contextual metadata tag based on the detected response to the active document. In some examples, the processor may generate a mood tag. For example, the mood tag may correspond to a detected mood of the user while reading or writing to the active document. In some examples, the processor may generate a movement tag. For example, the movement tag may indicate movement of a device while the active document was read or edited. For example, the movement tag may indicate whether or not the device was moving while the active document was being read or edited. In some examples, a movement tag may be generated based on detected eye movement of a user while accessing a document. For example, the user may have been reading the document multiple times or may have read portions of a document multiple times. In some examples, the user may have read a document or portion of a document for a longer period of time. For example, the period of time may be detected as exceeding a predetermined threshold period of time.

At block 308, the processor stores the contextual metadata tags. For example, the contextual metadata tags may be appended to corresponding active documents. In some examples, the processor may store the contextual metadata tags to a database.

At block 310, the processor receives a query including a contextual keyword corresponding to the contextual metadata tag. For example, the query may include text to search and one or more contextual keywords to use in filtering the search results as described below. In some examples, the processor may receive a query without any keyword and suggest one or more keywords in response to detecting that the number of search results for the query exceeds a predetermined threshold number of search results. For example, the processor may detect that a query for a document results in 52 documents. The predetermined threshold number of search results may be, for example, 20 documents. The processor may then suggest a set of filters to be applied. The user may then select a filter with a specific value for the filter. For example, the user may select a mood filter with a value of "angry." The processor may then filter the 52 documents based on detected angry mood. For example, the resulting filtered search results may include three documents associated with an angry mood.

At block 312, the processor filters search results received in response to the query based on the contextual metadata tag. For example, the filtered search results may contain search results that include contextual metadata tags corresponding to the contextual keyword.

At block 314, the processor displays a list of the filtered search results. For example, the list of filtered search results may include a list of filtered documents. In some examples, the filtered search results may also include a list of filters applied to the results. For example, the filtered search results may display whether the results were filtered based on mood, time, movement, documents read before or after, etc. In some examples, the specific value for each filter may also be displayed. For example, the mood filter may have been set to show documents associated with a surprised mood if the user remembers being surprised while previously reading a document to be retrieved. In some examples, the processor may receive additional contextual keywords in response to displaying the list of filtered search results. For example, the additional contextual keywords may be used to further filter the list of filtered search results and display an updated list of filtered search results.

The process flow diagram of FIG. 3 is not intended to indicate that the operations of the method 300 are to be executed in any particular order, or that all of the operations of the method 300 are to be included in every case. Additionally, the method 300 can include any suitable number of additional operations.

Figure 4:
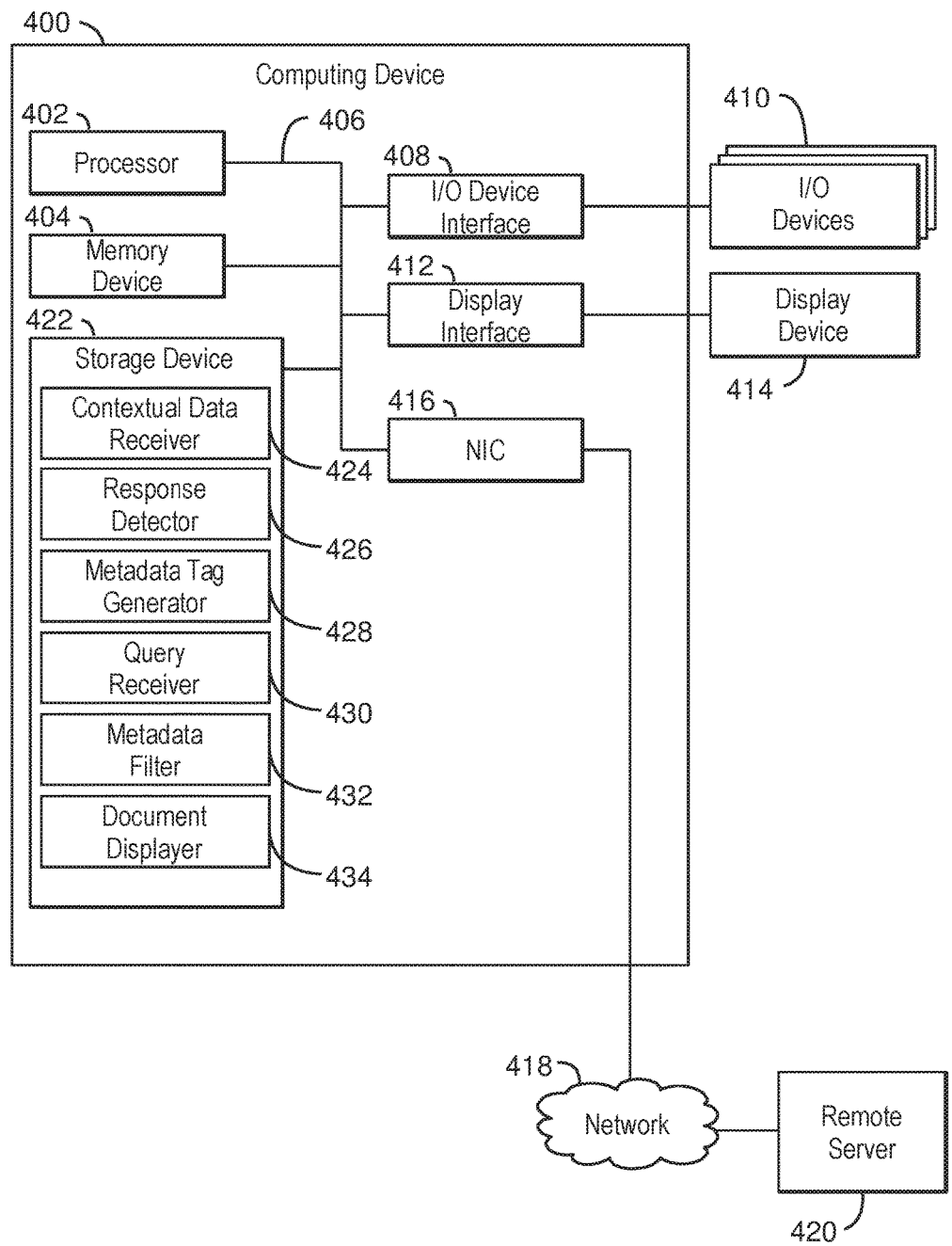
FIG. 4 is a block diagram of an example computing device that can filter document search results using contextual metadata.

With reference now to FIG. 4, an example computing device can filter document search results using contextual metadata. The computing device 400 may be for example, a server, a network device, desktop computer, laptop computer, tablet computer, or smartphone. In some examples, computing device 400 may be a cloud computing node. Computing device 400 may be described in the general context of computer system executable instructions, such as program modules, being executed by a computer system. Generally, program modules may include routines, programs, objects, components, logic, data structures, and so on that perform particular tasks or implement particular abstract data types. Computing device 400 may be practiced in distributed cloud computing environments where tasks are performed by remote processing devices that are linked through a communications network. In a distributed cloud computing environment, program modules may be located in both local and remote computer system storage media including memory storage devices.

The computing device 400 may include a processor 402 that is to execute stored instructions, a memory device 404 to provide temporary memory space for operations of said instructions during operation. The processor can be a single-core processor, multi-core processor, computing cluster, or any number of other configurations. The memory 404 can include random access memory (RAM), read only memory, flash memory, or any other suitable memory systems.

The processor 402 may be connected through a system interconnect 406 (e.g., PCI®, PCI-Express®, etc.) to an input/output (I/O) device interface 408 adapted to connect the computing device 400 to one or more I/O devices 410. The I/O devices 410 may include, for example, a keyboard and a pointing device, wherein the pointing device may include a touchpad or a touchscreen, among others. The I/O devices 410 may be built-in components of the computing device 400, or may be devices that are externally connected to the computing device 400.

The processor 402 may also be linked through the system interconnect 406 to a display interface 412 adapted to connect the computing device 400 to a display device 414. The display device 414 may include a display screen that is a built-in component of the computing device 400. The display device 414 may also include a computer monitor, television, or projector, among others, that is externally connected to the computing device 400. In addition, a network interface controller (NIC) 416 may be adapted to connect the computing device 400 through the system interconnect 406 to the network 418. In some embodiments, the NIC 416 can transmit data using any suitable interface or protocol, such as the internet small computer system interface, among others. The network 418 may be a cellular network, a radio network, a wide area network (WAN), a local area network (LAN), or the Internet, among others. An external computing device 420 may connect to the computing device 400 through the network 418. In some examples, external computing device 420 may be an external web-server 420. In some examples, external computing device 420 may be a cloud computing node.

The processor 402 may also be linked through the system interconnect 406 to a storage device 422 that can include a hard drive, an optical drive, a USB flash drive, an array of drives, or any combinations thereof. In some examples, the storage device may include a contextual data receiver module 424, a response detector module 426, a metadata tag generator module 428, a query receiver module 430, a metadata filter module 432, and a document displayer module 434. In some examples, one or more of the modules 424-434 may be implemented in an application or a web browser plugin. The contextual data receiver module 424 can receive contextual data including a facial movement associated with an active document. For example, the facial movement may be an eye movement, or other facial movement as described above. In some examples, the contextual data may also include an image of a face of a user reading the active document. In some examples, the contextual data may include a document accessed before or after the active document. In some examples, the contextual data may include the contextual data includes a time and global positioning satellite (GPS) information. The response detector module 426 can then detect a response associated with the active document based on the received contextual data. For example, the response may be an emotional response detected based on the contextual data. In some examples, the response may be a facial expression. The metadata tag generator module 428 can generate a contextual metadata tag based on the detected response to the active document. In some examples, the metadata tag generator module 428 can store the generated metadata tag appended to the active document. The query receiver module 430 can receive a query including a contextual keyword corresponding to the contextual metadata tag. In some examples, the contextual keyword may be one of a plurality of contextual keywords displayed in response to detecting that the search results received in response to the query exceed a predetermined threshold number of search results. The metadata filter module 432 can filter search results received in response to the query based on the contextual metadata tag. The document displayer module 434 can display a list of the filtered search results. For example, the filtered search results may include the document being searched for with less additional search results.

It is to be understood that the block diagram of FIG. 4 is not intended to indicate that the computing device 400 is to include all of the components shown in FIG. 4. Rather, the computing device 400 can include fewer or additional components not illustrated in FIG. 4 (e.g., additional memory components, embedded controllers, modules, additional network interfaces, etc.). Furthermore, any of the functionalities of the contextual data receiver module 424, the response detector module 426, the metadata tag generator module 428, the query receiver module 430, the metadata filter module 432, and the document displayer module 434, may be partially, or entirely, implemented in hardware and/or in the processor 402. For example, the functionality may be implemented with an application specific integrated circuit, logic implemented in an embedded controller, or in logic implemented in the processor 402, among others. In some embodiments, the functionalities of the contextual data receiver module 424, the response detector module 426, the metadata tag generator module 428, the query receiver module 430, the metadata filter module 432, and the document displayer module 434, can be implemented with logic, wherein the logic, as referred to herein, can include any suitable hardware (e.g., a processor, among others), software (e.g., an application, among others), firmware, or any suitable combination of hardware, software, and firmware.

Figure 5:
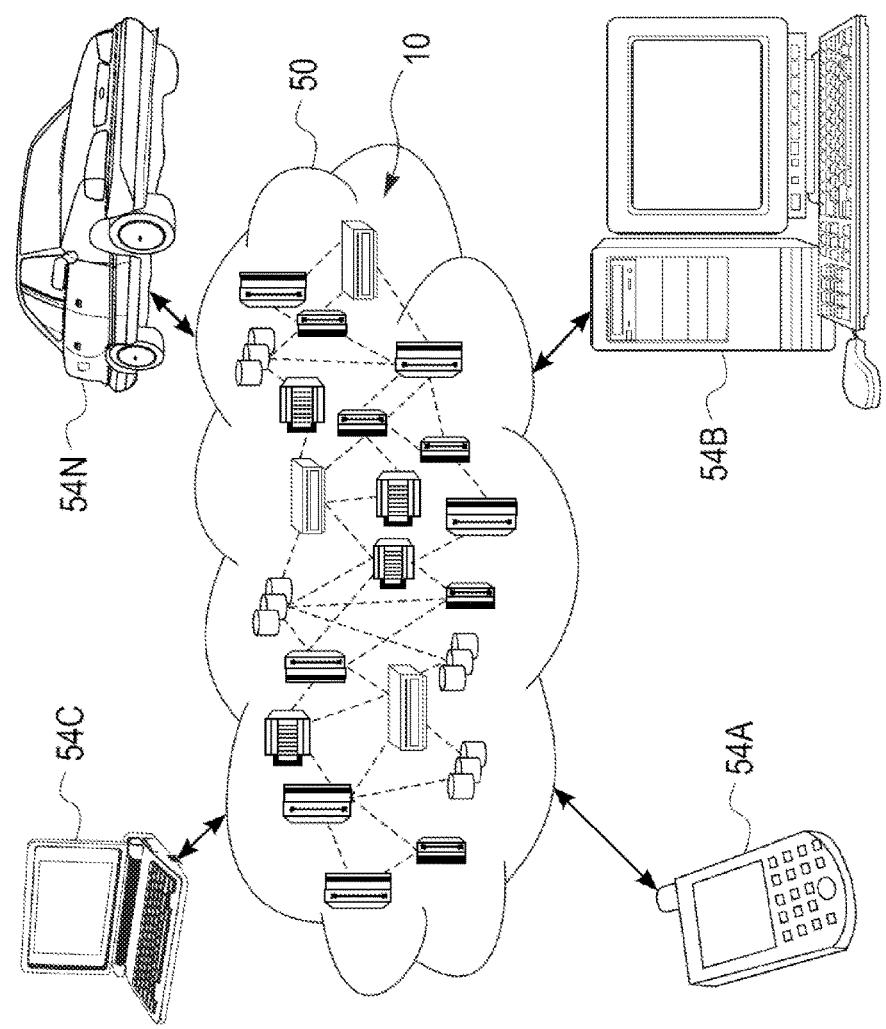
FIG. 5 is a block diagram of an example cloud computing environment according to embodiments described herein.

Referring now to FIG. 5, an illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 5 are intended to be illustrative only and that computing nodes 10 and cloud computing environment 50 can communicate with any type of computerized device over any type of network and/or network addressable connection (e.g., using a web browser).

Figure 6:
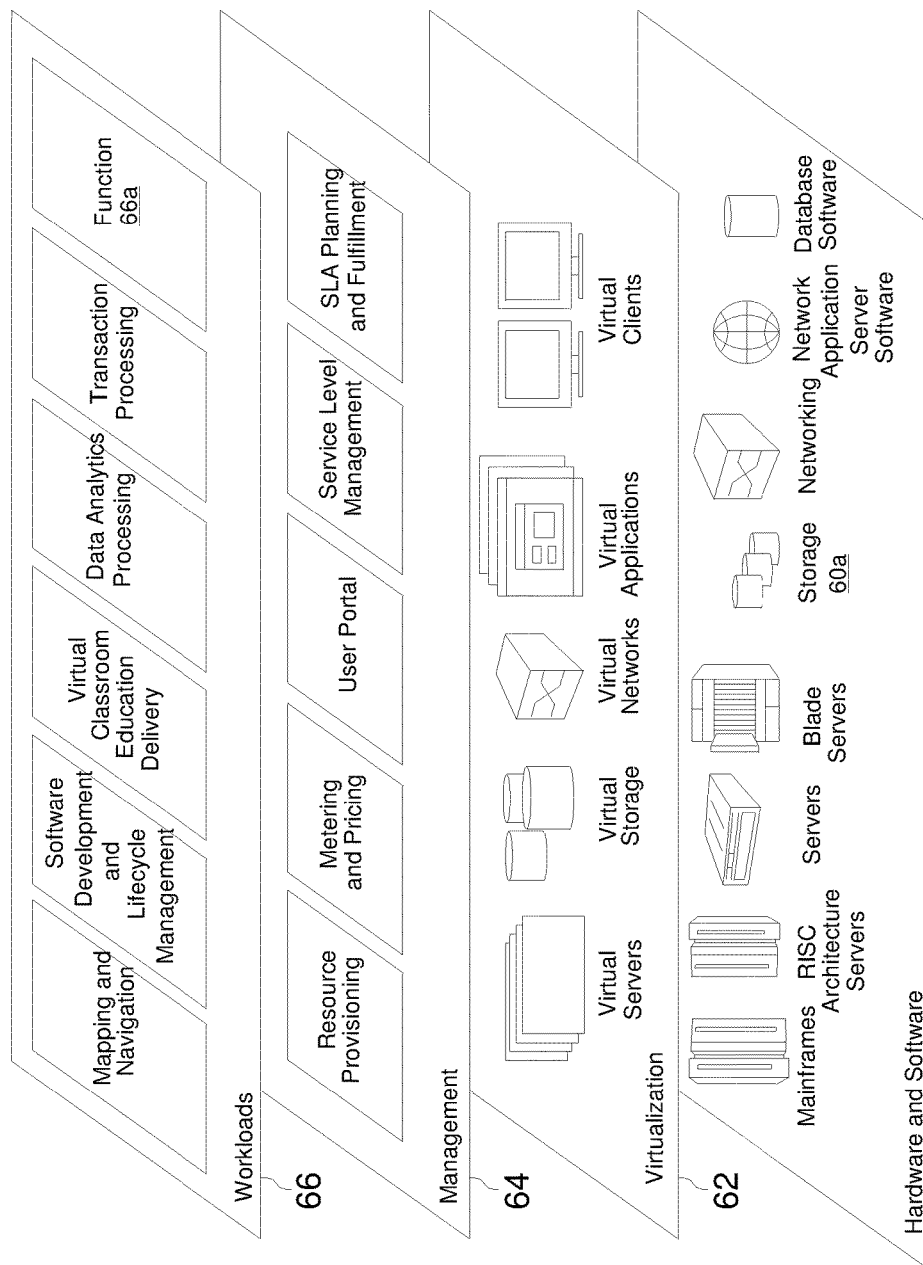
FIG. 6 is an example abstraction model layers according to embodiments described herein.

Referring now to FIG. 6, a set of functional abstraction layers provided by cloud computing environment 50 (FIG. 5) is shown. It should be understood in advance that the components, layers, and functions shown in FIG. 6 are intended to be illustrative only and embodiments of the invention are not limited thereto. As depicted, the following layers and corresponding functions are provided:

Hardware and software layer 60 includes hardware and software components. One physical location where a program to perform method 300 may be stored is in storage block 60a. Examples of hardware components include mainframes, in one example IBM® zSeries® systems; RISC (Reduced Instruction Set Computer) architecture based servers, in one example IBM pSeries® systems; IBM xSeries® systems; IBM BladeCenter® systems; storage devices; networks and networking components. Examples of software components include network application server software, in one example IBM WebSphere® application server software; and database software, in one example IBM DB2® database software. (Note: the terms "IBM", "zSeries", "pSeries", "xSeries", "BladeCenter", "WebSphere", and "DB2" may be subject to trademark rights in various jurisdictions throughout the world and are used here only in reference to the products or services properly denominated by the marks to the extent that such trademark rights may exist.)

Virtualization layer 62 provides an abstraction layer from which the following examples of virtual entities may be provided: virtual servers; virtual storage; virtual networks, including virtual private networks; virtual applications and operating systems; and virtual clients. In one example, management layer 64 may provide the functions described below. Resource provisioning provides dynamic procurement of computing resources and other resources that are utilized to perform tasks within the cloud computing environment. Metering and Pricing provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal provides access to the cloud computing environment for consumers and system administrators. Service level management provides cloud computing resource allocation and management such that required service levels are met. Service Level Agreement (SLA) planning and fulfillment provide pre-arrangement for, and procurement of, cloud computing resources for which a future requirement is anticipated in accordance with an SLA.

Workloads layer 66 provides examples of functionality for which the cloud computing environment may be utilized. Examples of workloads and functions which may be provided from this layer include: mapping and navigation; software development and lifecycle management; virtual classroom education delivery; data analytics processing; transaction processing; and contextual document retrieval.

The present invention may be a system, a method or computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD- ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the present invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

Figure 7:
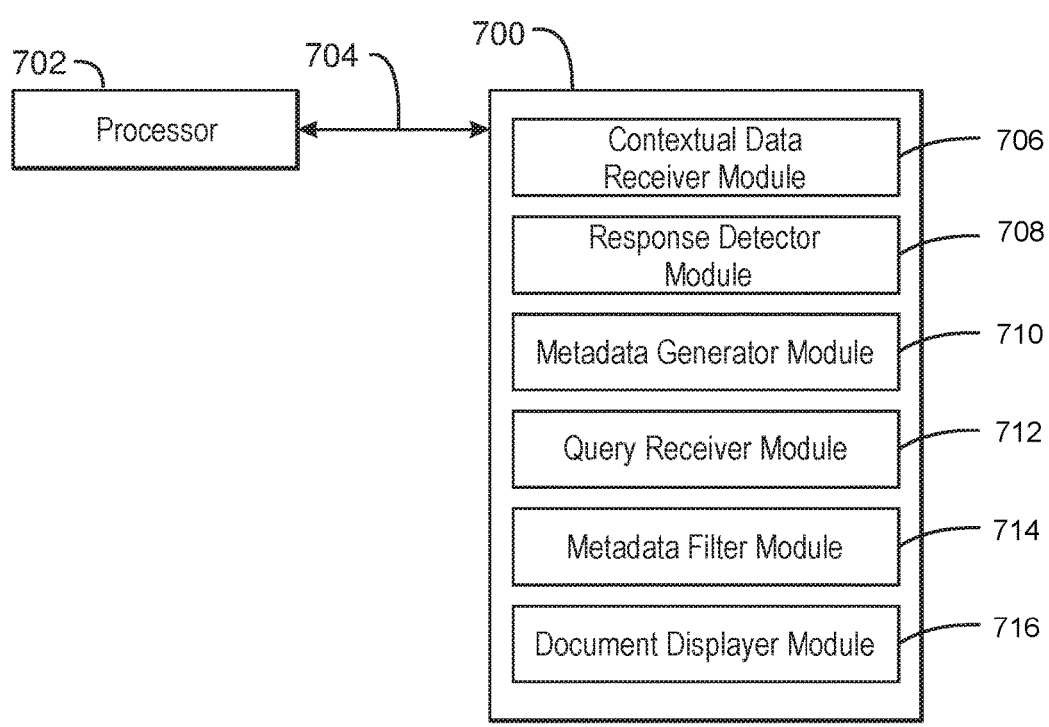
FIG. 7 is an example tangible, non-transitory computer-readable medium that can filter document search results using contextual metadata.

Referring now to FIG. 7, a block diagram is depicted of an example tangible, non-transitory computer-readable medium 700 that can filter document search results using contextual metadata. The tangible, non-transitory, computer-readable medium 700 may be accessed by a processor 702 over a computer interconnect 704. Furthermore, the tangible, non-transitory, computer-readable medium 700 may include code to direct the processor 702 to perform the operations of the method 300 of FIG. 3 above.

The various software components discussed herein may be stored on the tangible, non-transitory, computer-readable medium 700, as indicated in FIG. 7. For example, a contextual data receiver module 706 includes code to receive contextual data including a facial movement associated with an active document. For example, the facial movement may be an eye movement. In some examples, the contextual data may also include a document accessed before or after the active document, a time, a global positioning satellite (GPS) location, or any combination thereof. A response detector module 708 includes code to detect a response associated with the active document based on the received contextual data. For example, the response may be an emotion response detected based on the contextual data. The response detector module 708 may also include code to detect movement using time and GPS location data. A metadata generator module 710 includes code to generate a contextual metadata tag based on the detected response to the active document. In some examples, the metadata generator module 710 may include code to generate a contextual metadata tag for the active document based on a previously active document and a subsequently active document. In some examples, the metadata generator module 710 may include code to generate a mood tag based on the contextual data, wherein the contextual data further includes images of a face associated with the active document. In some examples, the metadata generator module 710 may include code to generate a movement tag in response to detecting a change in location of a device displaying the active document. A query receiver module 712 includes code to receive a query including a contextual keyword corresponding to the contextual metadata tag. A metadata filter module 714 includes code to filter search results received in response to the query based on the contextual metadata tag. In some examples, the metadata filter module 714 may include code to display categories of contextual metadata tags in response to detecting that the filter search results exceed a predetermined threshold. A document displayer module 716 includes code to display a list of the filtered search results. In some examples, the list of filtered search results may include the document that was active under the contextual conditions specified via the metadata keyword. It is to be understood that any number of additional software components not shown in FIG. 7 may be included within the tangible, non-transitory, computer-readable medium 700, depending on the particular application.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Some helpful definitions follow:

Present invention: should not be taken as an absolute indication that the subject matter described by the term "present invention" is covered by either the claims as they are filed, or by the claims that may eventually issue after patent prosecution; while the term "present invention" is used to help the reader to get a general feel for which disclosures herein that are believed as maybe being new, this understanding, as indicated by use of the term "present invention," is tentative and provisional and subject to change over the course of patent prosecution as relevant information is developed and as the claims are potentially amended.

Embodiment: see definition of "present invention" above—similar cautions apply to the term "embodiment."

and/or: inclusive or; for example, A, B "and/or" C means that at least one of A or B or C is true and applicable.

User/subscriber: includes, but is not necessarily limited to, the following: (i) a single individual human; (ii) an artificial intelligence entity with sufficient intelligence to act as a user or subscriber; and/or (iii) a group of related users or subscribers.

Module/Sub-Module: any set of hardware, firmware and/or software that operatively works to do some kind of function, without regard to whether the module is: (i) in a single local proximity; (ii) distributed over a wide area; (iii) in a single proximity within a larger piece of software code; (iv) located within a single piece of software code; (v) located in a single storage device, memory or medium; (vi) mechanically connected; (vii) electrically connected; and/or (viii) connected in data communication.

Computer: any device with significant data processing and/or machine readable instruction reading capabilities including, but not limited to: desktop computers, mainframe computers, laptop computers, field-programmable gate array (FPGA) based devices, smart phones, personal digital assistants (PDAs), body-mounted or inserted computers, embedded device style computers, application-specific integrated circuit (ASIC) based devices.

What is claimed is:

1. A computer-implemented method for filtering document search results, the computer-implemented method comprising:
    receiving contextual data comprising a facial movement associated with an active document, an image of a face of a user reading the active document, a location where the user read the active document, a timestamp indicating when the user read the active document; and a timestamp indicating when the user edited the active document, wherein the contextual data is based, at least in part, on physical contexts of the user, wherein the physical contexts include movement of hands, movement of eyes, posture of the user, motion of the user's body, location of the user, facial expressions, identities of people proximate the user, and environmental characteristics;
    detecting an emotional response associated with the active document based on the contextual data, wherein the emotional response is detected based, at least in part, on the shape and position of the mouth, nose, eyebrows, and facial lines in the forehead in relation to one another;
    generating a contextual metadata tag based on the contextual data and the detected response to the active document, the contextual metadata tag including a movement tag indicating a movement of a device while the active document was read by the user and a movement of the device while the active document was edited by the user;
    receiving a query comprising a contextual keyword corresponding to the contextual metadata tag;
    filtering search results received in response to the query based on the contextual metadata tag; and
    displaying a list of the filtered search results.

* * * * *